United States Patent [19]

Kelly

[11] 4,032,542

[45] June 28, 1977

[54] 4α,6-DIHYDROXY-5-IODO-2β-ARYLOX-YMETHYL-3α-TETRAHYDROPYRANOA-CETIC ACID γ-LACTONE, 6-ALKYL ETHERS

[75] Inventor: Robert C. Kelly, Kalamazoo, Mich.

[73] Assignee: The Upjohn Company, Kalamazoo, Mich.

[22] Filed: Apr. 14, 1976

[21] Appl. No.: 676,895

[52] U.S. Cl. .............................. 260/343.6; 260/343; 260/343.3 R; 260/343.5; 260/345.7; 260/345.8; 260/395; 260/468 D; 260/479 S; 260/483; 260/514 D; 260/535 R; 424/283

[51] Int. Cl.² ...................................... C07D 493/04

[58] Field of Search ............................... 260/343.6

[56] References Cited

UNITED STATES PATENTS 3,806,540   4/1974   Martel .................... 260/486 H Primary Examiner—Cecilia M. Jaisle
Attorney, Agent, or Firm—Robert A. Armitage

[57] ABSTRACT

The present specification provides novel intermediates and novel processes for the synthesis of Thromboxane $B_2$ (11a-homo-11a-oxa-PGF$_2\alpha$ ), its 15-epimer, and various carboxyl derivatives thereof. In particular, there are disclosed various bicyclic tetrahydropyran-containing lactones useful in the above processes, and corresponding acyclic lactones.

2 Claims, No Drawings

4α,6-DIHYDROXY-5-IODO-2β-ARYLOXYMETHYL-3α-TETRAHYDROPYRANOACETIC ACID γ-LACTONE, 6-ALKYL ETHERS

The present invention relates to thromboxane $B_2$ and associated intermediates and processes for which the essential material constituting a disclosure therefor is incorporated by reference here from Ser. No. 676,890, filed Apr. 14, 1976, now pending issuance as a United States Patent.

I claim:

1. A thromboxane intermediate of the formula

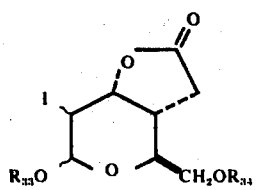

wherein $R_{34}$ is an arylmethyl hydroxy-hydrogen replacing group selected from the group consisting of
   a. benzyl,
   b. benzyl substituted by one to five alkyl of one to four carbon atoms, inclusive, chloro, bromo, iodo, fluoro, nitro, phenylalkyl of 7 to 12 carbon atoms, inclusive,
   c. benzhydryl,
   d. benzhydryl substituted by one to ten alkyl of one to four carbon atoms, inclusive, chloro, bromo, iodo, fluoro, nitro, phenylalkyl to 7 to 12 carbon atoms, inclusive,
   e. trityl, and
   f. trityl substituted by one to 15 alkyl of one to four carbon atoms, inclusive, chloro, bromo, iodo, fluoro, nitro, phenylalkyl of 7 to 12 carbon atoms, inclusive;
   and wherein $R_{33}$ is alkyl of one to 5 carbon atoms, inclusive.

2. 6α- or 6β-methoxy-5β-iodo-4α-hydroxy-2β-benzyloxymethyl-3α-tetrahydrofuran acetic acid, γ-lactone, a thromboxane intermediate according to claim 1.

* * * * *